United States Patent [19]

Shimizu

[11] Patent Number: 5,190,086
[45] Date of Patent: Mar. 2, 1993

[54] MEDICAMENT SUPPLY APPARATUS FOR USE IN ELUTION TESTING DEVICE

[75] Inventor: Yasunori Shimizu, Nagaokakyo, Japan

[73] Assignee: Dainippon Seiki Co., Ltd., Kyoto, Japan

[21] Appl. No.: 743,620

[22] Filed: Aug. 12, 1991

[30] Foreign Application Priority Data

Aug. 20, 1990 [JP] Japan .................. 2-87276[U]

[51] Int. Cl.$^5$ .................. B65B 31/00; B67C 3/00
[52] U.S. Cl. .................. 141/174; 141/168; 414/419
[58] Field of Search .............. 141/165, 168, 171, 174, 141/175, 176, 129, 173, 83, 99, 234, 239, 241; 414/419, 421

[56] References Cited

U.S. PATENT DOCUMENTS 2,386,152 10/1945 Wahl .................. 141/174
2,726,779 12/1955 Kendall .................. 414/419
3,458,070 7/1969 Moore et al. .................. 414/421

FOREIGN PATENT DOCUMENTS 63-196859 8/1988 Japan .................. 141/168

Primary Examiner—Henry J. Recla
Assistant Examiner—Steven O. Douglas
Attorney, Agent, or Firm—Lowe, Price, LeBlanc & Becker

[57] ABSTRACT

An apparatus for automatically supplying a medicament into a container comprising a mechanism having a plurality of separate small medicament cups each containing a medicament so that the medicament may be supplied from the medicament cup to a test container for use in an elution testing device. The small medicament cups each containing a medicament is moved linearly one after another to a medicament supply position and placed on the position to be once held there then turned, whereby the medicament contained in the medicament cup is dropped out of an opening formed on upper end face of the cup.

4 Claims, 3 Drawing Sheets

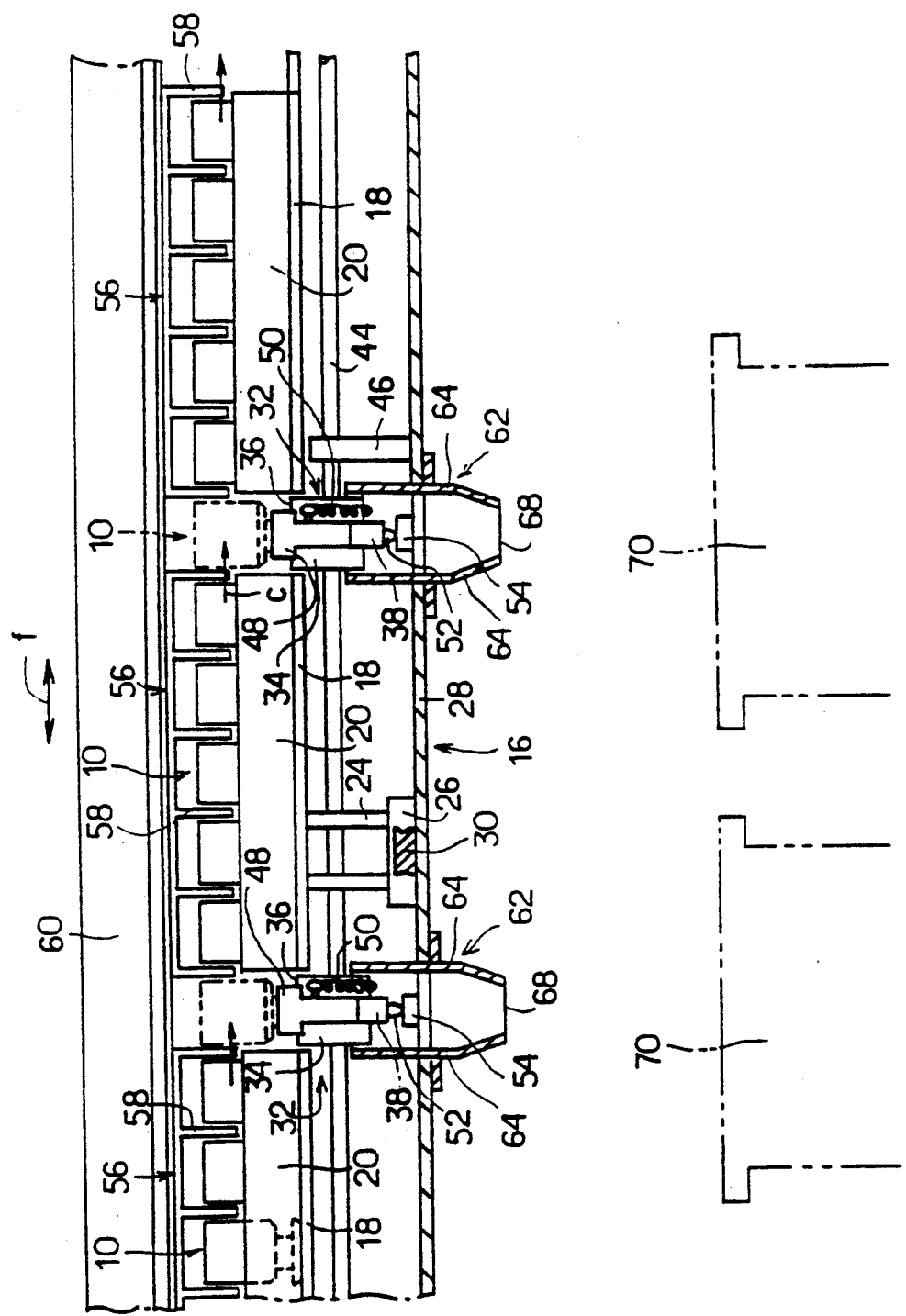

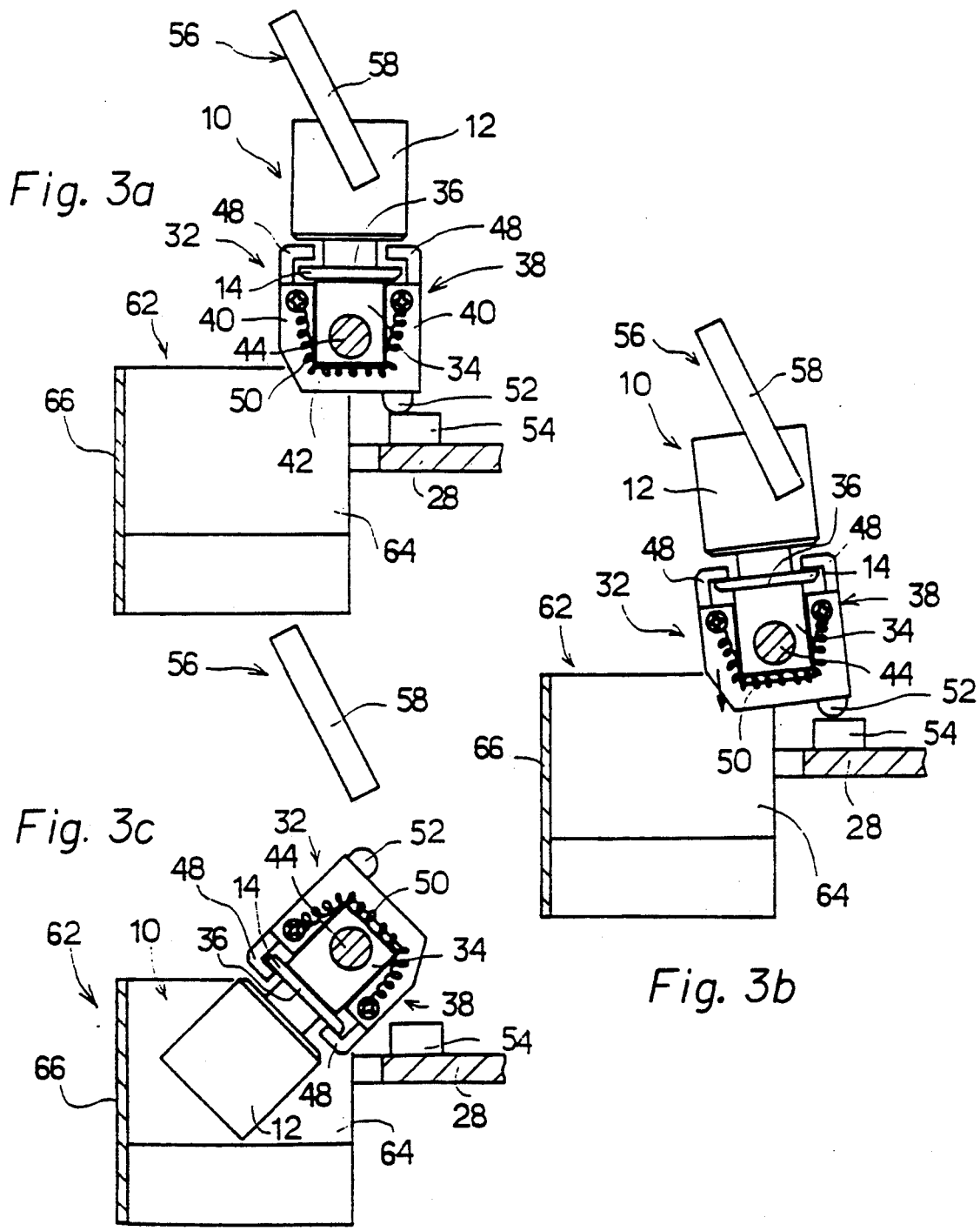

MEDICAMENT SUPPLY APPARATUS FOR USE IN ELUTION TESTING DEVICE

BACKGROUND OF THE INVENTION

1. Field of the invention:

The present invention relates to an apparatus for automatically supplying a test medicament into an elution test container containing a test liquid (solvent) for use in elution testing device for measuring elution degree of components of solid medicaments in forms of tablets, granule, capsule and so on when dipping them in the solvent.

2. Description of Prior Art:

Recently, elution test of solid medicaments such as tablets, granules, capsules, etc., has been regarded important as one of medicament quality evaluation methods. Such elution test is carried out to measure elution rate of main medicine of solid medicament when dipping it in various solvents. In such elution test, for example, a solid medicament is first dipped into various solvents each put in a test container and kept at a temperature of 37° C., then a certain quantity of solution is periodically picked up as a sample liquid of which absorbancy is measured with a spectrophotometer one after another, and thus changes of elution quality of main medicine are recorded by time elapse While, to measure several components of a medicament simultaneously, a certain quantity of sample liquid is separately picked up and liquid chromatographic analysis is conducted on them.

In the mentioned method of elution test, a glass container having a semiglobular inner bottom surface with a radius of 50 to 52.5 mm and an open upper end surface and having a capacity of 1,000 ml is employed. 500 to 900 ml of test liquid (solvent) is poured into the test container, then a test medicament is dipped into the test liquid to be dissolved therein. In this method, the step of pouring a test liquid into a test container has been heretofore performed manually.

To avoid such a troublesome manual work, for example, the Japanese Patent Publication (unexamined) No. 63-196859 has disclosed a turntable for supplying sample medicaments into containers one after another from sample holes through sample injection slots. To carry out such supplying operation using the turntable, an upper disc provided with a plurality of sample holes in circumferential direction is coaxially superposed on a lower disc provided with sample injection slots, then the upper disc is rotated with respect to the lower disc so that each sample hole on which sample medicament is placed is moved to the location of a sample injection slot one after another.

However, it is troublesome to supply test medicament manually into a test container and, in particular, those manually worked become further troublesome when number of test containers increases, for example, to six. There is a further possibility of occurring any artificial mistake such as one in weighing. In this respect, it is a recent trend to automatically carry out every process of various tests, and in this sense manual supply of test medicament is undoubtedly a drawback to be overcome in view of full automation.

In the medicament supply apparatus of turntable type as is disclosed in the Japanese Laid-Open Patent Publication (unexamined) No. 63-196859, a problem exists in that cleaning of medicament tray part and inner peripheral surface of sample holes is quite troublesome, eventually making it very difficult to perform the entire maintenance. Another problem exists in that it is impossible to supply granular medicament. In case of installing plural test containers, a further problem exists in that a turntable for each test container and plural control mechanisms are required to control each table separately.

SUMMARY OF THE INVENTION

The present invention was made to solve the above-discussed problems and has an object of providing an apparatus for supplying a medicament in which maintenance such as cleaning is easy and any type of medicament, irrespective of shape thereof, can be exactly and automatically supplied to a test container, said apparatus being capable of supplying medicament simultaneously to a plurality of test containers just by a single drive source and controller.

To accomplish the foregoing object, an apparatus for automatically supplying a medicament into a container essentially comprises a mechanism having a plurality of separate small cups each containing medicament so that the medicament may be supplied from the medicament cup to a test container for use in an elution testing device; said small cups each containing a medicament being moved linearly one after another to a medicament supply position and placed on that position to be once held there then turned, whereby the medicament contained in the medicament cup is dropped out of an opening formed on upper end face of the medicament cup. More specifically, the apparatus for automatically supplying medicament according to the present invention comprises: a plurality of medicament cups each containing a measured quantity of medicament therein, each cup having an opening on upper end face and a portion to be engaged on lower part; horizontal tables on which said plurality of medicament cups are placed in a row; guide members respectively disposed along the row of the plurality of medicament cups placed on said horizontal tables; rotating members disposed adjacent front end of said row on said horizontal table, each rotating member having a holding face formed so as to have a height almost the same as upper face of the horizontal table and a passage continuous in association with the upper face of the horizontal table and having engaging means for engaging with said portion to be engaged of each medicament cup; a horizontal support shaft which is fixed to said rotating members and supported rotatably so as to turn the rotating members 90° forward simultaneously within a vertical surface perpendicular to direction of the row of said medicament cups; a turning mechanism for turning said horizontal supporting shaft; and a direct acting mechanism which engages with said plurality of cups on respective horizontal tables placed on respective horizontal tables, moves the medicament cups in one direction linearly along said guide members while sliding external bottom face of each medicament cup on upper face of the horizontal table, whereby the plurality of medicament cups on the horizontal tables are delivered one by one onto the holding face of each rotating member.

It is preferable that each of the mentioned medicament cups is provided with a flat leg part so that each rotating member is provided with means for holding a medicament cup by grasping the flat leg part. That is, it is preferable that each rotating member comprises: a holding block having a holding face and to which horizontal supporting shaft is fixed; an engaging member in which two side walls opposed in parallel to each other and a bottom wall connecting the two side walls are solidly formed to have a ⊐-shaped opening on upper part, and retaining claws in parallel to each other of hook shape in section and protruding toward opposite sides are also solidly formed, whereby the engaging member engages with said holding block from outside in such a manner that said retaining claws are in parallel to said horizontal supporting shaft and that the engaging member be vertically slidable along side face of the holding block; spring means for urging said engaging member downward with respect to said holding block; and a contact member for pushing said engaging member upward with respect to said holding block against spring force of said spring means at the time of erecting the rotating members so as to form a gap for insertion of flat leg part of said medicament cup between said retaining claws of the engaging members and said holding face of the holding block.

It is also preferable to provide a guide member of which lower end face is open at a location right above the upper end opening of the test container disposed on lower part and into which medicament is injected, said guide member comprising two side guide walls which are disposed on front side of each rotating member in parallel to a turning face of each rotating member and having a width slightly larger than that of a medicament cup turning while being kept by the rotating member; and a front shielding wall formed continuously on said two side guide walls.

In the medicament supply apparatus of above arrangement, a medicament is weighed and placed in each medicament cup, and the medicament cups each containing the medicament are placed on the horizontal table in a row. The plurality of medicament cups are then transferred by the direct acting mechanism in such a manner that outer bottom face of each medicament cup is linearly moved along the guide member while sliding on the upper face of the horizontal table. Thus, one of the plurality of medicament cups is delivered onto the holding face of the rotating member disposed adjacent the front end of the horizontal table. In this step, since height of the holding face of the rotating member is almost the same as the upper face of the horizontal table, the medicament cup is transferred smoothly from the horizontal table to the rotating member. The medicament cup transferred on the holding face of the rotating member is held thereon by the engaging means of the rotating member which engages with a part to be engaged at lower part. Thereafter, when turning the horizontal supporting shaft by the turning mechanism thereby turning the rotating member over 90° forward within a vertical surface, the open upper end face of the medicament cup is directed downward and the medicament contained in the cup drops out of the cup from the open upper end face, whereby the medicament is supplied into the test container disposed beneath the cup.

In effect, in the mentioned apparatus for supplying medicament, a medicament is contained in an independent medicament cup and thrown in a test container therefrom. Therefore, cleaning of medicament cup can be easily performed by removing the cup from the horizontal table. It is also possible to supply granular medicament. Further, in this medicament supply apparatus, by arranging several pairs of horizontal tables and rotating members linearly in a row, it becomes possible to perform supply of medicament into a plurality of test containers simultaneously at once.

Furthermore, when disposing the guide member having the mentioned two side guide walls and front shielding wall on the front side of the rotating member, medicament is exactly introduced into test container by the guide member.

In the apparatus for supplying medicament of above arrangement and function, not only maintenance such as cleaning is easy but also any medicament including granule can be exactly and automatically supplied into test container, irrespective of type of medicament. Moreover, as a result of arranging plural pairs of horizontal tables and rotating members linearly in a row, simultaneous supply of medicament into plural test containers can be performed. Finally, the apparatus of the invention provides full automatic process of elution test.

Other objects and advantages of the invention will become apparent in the course of following description with reference to the accompanying drawings.

BRIEF DESCRIPTION OF THE DRAWINGS

FIG. 2 is a longitudinal sectional view thereof; and

FIGS. 3(a), (b) and (c) are partially sectional side views of the rotating member respectively for explaining medicament supply operation.

DESCRIPTION OF THE PREFERRED EMBODIMENT

Figure 1:
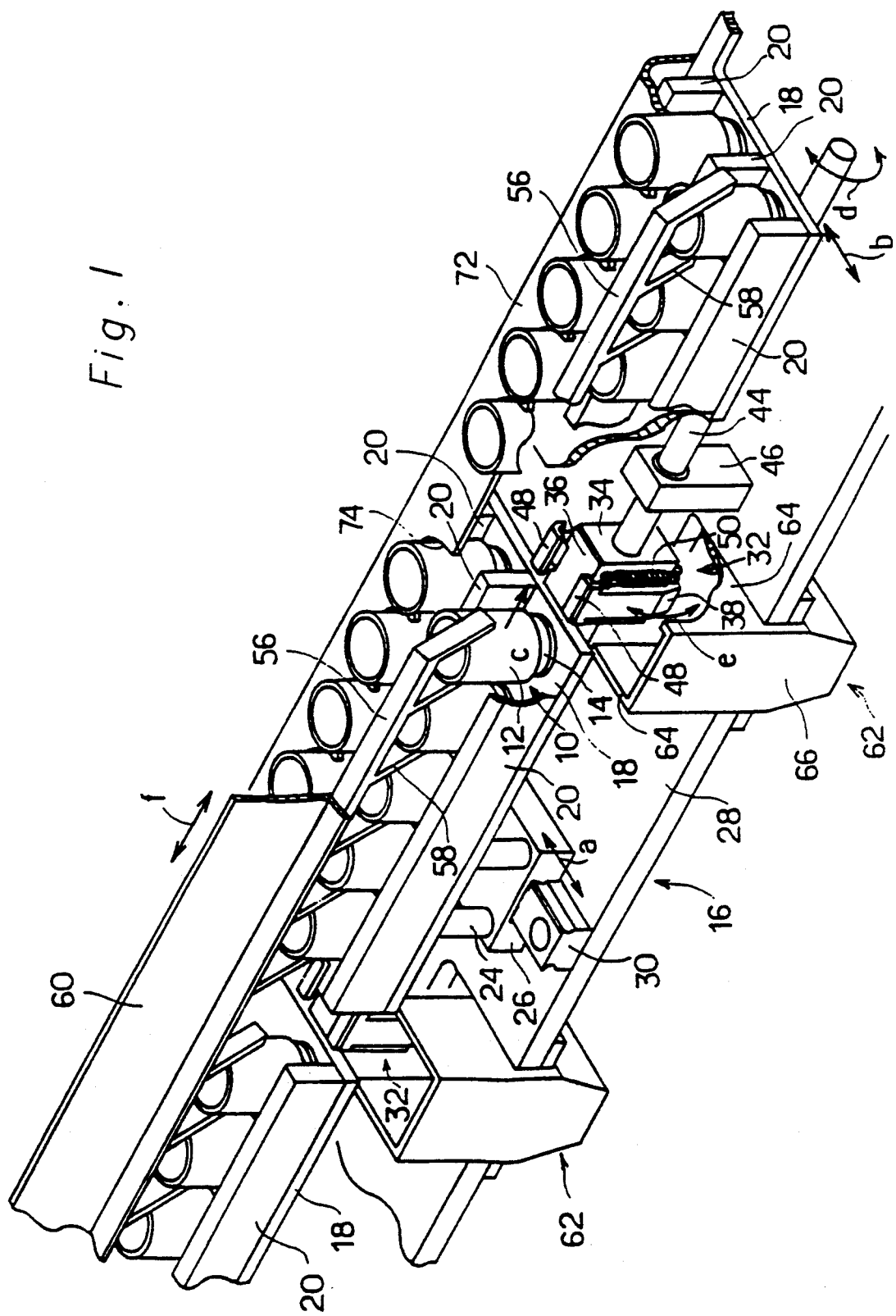
FIG. 1 is a partially broken perspective view of an essential part of the medicament supply apparatus for use in elution testing device according to one embodiment of the present invention.

An embodiment according to the present invention is hereinafter described with reference to the drawings.

FIGS. 1 and 2 both show an embodiment of the invention, and in which FIG. 1 is a partially broken perspective view of an essential part of the medicament supply apparatus for use in elution testing device, and FIG. 2 is a longitudinal sectional view thereof.

As shown in the drawings, in the medicament supply apparatus of this embodiment, a medicament cup 10 is employed and in which a leg portion having a disc part 14 is solidly formed at the lower part of a cylindrical medicament cup containing part 12 with open top end and flat bottom. And in the main body 16, a plurality of horizontal tables 18 to put the medicament cup 10 on are arranged in a row in such a manner as to be partially connected with each other. On one horizontal table 18, two rows of medicament cups 10, each row being formed of five cups, are disposed. On this horizontal table 18, three guide plates 20 are arranged in parallel to each other at an interval little wider than diameter or width of a medicament cup 10 along the row of the medicament cup 10. The horizontal table 18 is supported on a bed 28 through a plurality of columns 24 fixed to the lower face of the bed and a sliding base plate 26 to which the columns 24 are fixed. Further, the sliding base plate 26 is slidably engaged with a guide rail 30 fixed onto the upper face of the bed 28 so as to slide on the bed 28 forward and backward (in the direction indicated by the arrow "a") guided by the guide rail 30, thereby moving forward and backward respective horizontal tables 18 integrally with the sliding base plate 26 (in the direction indicated by the arrow "b").

Between one horizontal table 18 and another 18 adjacent thereto, a rotating member 32 is disposed adjacent to front end of the one horizontal table 18. The rotating member 32, as shown in FIG. 3 illustrating a side view thereof, is composed of a holding block 34 having a holding face 36 to put the mentioned cups 10 on and hold it, and a ⊐-shaped engaging member 38 with open upper part in which both side walls 40, 40 and bottom wall 42 connecting those two side walls 40, forming one body. The holding block 34 is fixed to and supported by a horizontal shaft 44 with the holding face 36 having almost the same height as upper face of the horizontal table 18 so as to form a continuous passage communicating with the upper face of the horizontal table 18 when the rotating member is in the upright position. The horizontal shaft 44 is disposed in parallel to the horizontal table 18, is supported rotatably by a bearing 46 fixed to the bed 28, and is connected to a drive mechanism not illustrated. Thus, rotation of the horizontal shaft 44 in the direction of the arrow "d" by the drive mechanism enables the horizontal shaft 44 to turn the rotating member 32 fixed to the holding block 34 over 90° forward (in the direction of the arrow "e") within a vertical surface intersecting the row of the medicament cups 10 at right angle.

Arranged solidly at each top end of the two side walls 40, 40 of the engaging member 38 are retaining claws 48, 48 being a hook-shape in section and projecting oppositely to each other. Each of the retaining claws 48, 48 is disposed in parallel to the horizontal shaft 44 along the moving direction of the medicament cups 10 (in the direction of the arrow "c"). Interval between the projecting top ends of the two retaining claws 48, 48 is established to be shorter than diameter of the disc part 14 of the leg portion of the medicament cup 10. On the other hand, interval between the internal surfaces of concave portions of the two retaining claws, 48, 48 is established to be longer than diameter of the disc part 14 of the leg portion of the medicament cup 10. The mentioned engaging member 38 engages so as to slide vertically along the side of the holding block 34. Attached to this engaging member 38 is a tension spring 50 by which engaging member 38 is urged downward with respect to the holding block 34. Two ends of the tension spring 50 are respectively fixed to side faces of two side walls 40, 40 of the engaging member 38 and stretched over the bottom face of the holding block 34. Further, a projection 52 is solidly formed near rear end of the bottom wall 42 of the engaging member 38. On the other hand, a contactor 54 is formed on the upper side of the bed 28 so that when the rotating member 32 is in a state of standing upright or erected, the engaging member 38 receives upward pushing force from the contactor 54 on the bed 28 through the projection 52, thereby the engaging member 38 is pushed upward with respect to the holding block 34 against spring force of the tension spring 50 as shown in FIG. 3(a). In this state, a gap for inserting the leg disc 14 of the medicament cup 10 is formed between the retaining claw 48 of the engaging member 38 and the holding face 36 of the holding block 34.

Also arranged above the upper surface of each horizontal table 18 in parallel to the same is a horizontal arm 56 with six picking arms 58 in parallel to each other at intervals enough to get smoothly into the demicament containing part 12 of the respective medicament cups 10, and each horizontal arm 56 is fixed to a common drive plate 60. Thus, by moving said drive plate 60 linearly in the direction indicated by the arrow "f" in parallel to the horizontal table 18 by means of a linear motion mechanism (not illustrated) connected to the drive plate 60, the five medicament cups 10 supported by the horizontal arm member 56 through the six picking arms 58 are moved along the guide plate 20 with their external bottom side sliding on the upper face of the horizontal table 18, and one of those five medicament cups 10 is sent onto the holding face 36 of the holding block 34 of the rotating member 32. For sending medicament cups 10 on and after the second one (except the first cup) from right of the five medicament cups 10 onto the rotating members 32, the medicament cups 10 located at the right of the one is moved through the holding face 36 of the holding block 34 of the rotating member 32 onto the other adjacent horizontal table 18. The several picking arms 58 of the horizontal arm member 56 are so made as to be enough to get smoothly into the medicament containing part 12 of respective medicament cups 10. Therefore, for turning forwardly the medicament cups 10 supported by the rotating member 32 (in the direction of the arrow "e") within the vertical surface intersecting the row of the medicament cups 10 at right angle, there is no possibility that their turning is inhibited by the picking arms 58.

Disposed on the front side of the rotating member 32 is a guide member 62 consisting of two-side guide walls 64, 64 opposed to each other in parallel to rotation face of the rotating member 32 and a forward shielding wall 66 formed in continuation to the two-side guide walls 64, 64. A lower end face 68 of the guide member 62 has an opening right above the upper end opening face of the medicament cup 10. Interval between these two-side guide walls 64, 64 is a little wider than width of a medicament cup 10 so that the cup supported and turned by the rotating member 32 may not be inhibited from the rotation and that rotation of the cup may be guided. Disposed on the rear part of the horizontal table 18 is a positioning plate 72 possessing several positioning holes 74 respectively cut into semicircular shapes along peripheral contour of the medicament cups 10 corresponding to the row of the cups 10.

Described now is function of the medicament supply apparatus of above arrangement.

First, medicament is manually weighed and placed into each of the medicament cups 10, then the plural medicament cups 10 filled with medicament are placed on the horizontal table 18 in a row. Then, keeping the state shown in FIG. 1, the horizontal arms 56 is moved rightward through the drive plate 60 by means of a direct acting mechanism not illustrated, whereby several medicament cups 10 on the front row supported by the horizontal arm 56 through the picking arms 58 are transferred rightward along the guide plate 20 while sliding the lower face of the leg disc part 14 of each medicament cup 10 on the upper face of the horizontal table 18. In this manner, five medicament cups 10 forming a group located on the most right side are delivered from the horizontal table 18 onto the holding face 36 of the holding block 34 of the rotating member 32. In this step, the rotating member 32 is supported upright as shown in FIG. 3(a), and the leg disc part 14 of the medicament cup 10 is put between the retaining claw 48 of the engaging member 38 of the rotating member 32 and the holding face 36 of the holding block 34 as described above.

Subsequently, when turning the horizontal shaft 44 leftward by a turning mechanism not illustrated, a force received by the engaging member 38 from the contactor 54 through the projection 52 is gradually reduced and comes to permit separation of the projection 52 from the contactor 54, whereby the engaging member 38 slides downward with respect to the holding block 34 due to restoring force of the tension spring 50, as shown in FIG. 3(b). Accordingly, the leg disc part 14 of the medicament cup 10 is held between the holding face 36 of the holding block 34 and the retaining claws 48, 48 by the spring force of the tension spring 50, thus the medicament cups 10 being exactly secured to the holding block 34.

Then, as shown in FIG. 3(c), the horizontal shaft 44 and rotating member 32 are rotated to turn the medicament cup 10 counter-clockwise thereby directing the upper end opening of the cup downward. As a result, the medicament drops off the medicament containing section 12 and received by the test container 70 (see FIG. 2) disposed thereunder. At this time, since the guide member 62 is disposed on the front side of the rotating member 32, the medicament is securely introduced into the test container 70 without scattering about. Upon completion of medicament supply operation, the rotating mechanism turns the horizontal shaft 44 clockwise to return to the position shown in FIG. 3 (a).

After completing the supply of medicament into the test container 70 and the required elution test as to the medicament as described above, a medicament cup 10 second from right is then transferred to a predetermined position of the rotating member 32, and another supply of medicament into this cup takes place in the same manner as described with reference to FIGS. 3(a) to 3(c). When repeating the supply of medicament from each medicament cup 10 one after another thereby all five medicament cups 10 being empty, the sliding plate 26 slides forward on the bed 28 along the guide rail 30 by means of a drive mechanism not illustrated, whereby the horizontal table 18 coupled with the sliding plate 26 through the supporting column 24 is moved forward. As a result, another five medicament cups 10 located on the rear row are held by the picking arms 58 in place of the preceding empty five medicament cups 10 on the front row, and thereafter medicament supply operation being repeated in the same manner as described above.

The medicament supply apparatus according to the invention of above arrangement is not limited to the foregoing description and drawings, and may be embodied in other specific forms without departing from the spirit and scope of the invention. For example, although plural pairs of horizontal table and rotating member are linearly disposed in a row in the foregoing embodiment, it is also preferable that the medicament supply apparatus comprises only a single pair of them. Further, the engagement mechanism of medicament cup by means of the rotating member is not limited to the foregoing, and various changes and modifications may be made for those skilled in the art. Furthermore, the guide member disposed on front side of the rotating member is not always necessary as far as medicament is exactly thrown in test container from medicament cup.

What is claimed is:

1. An apparatus for automatically supplying medicament comprising,
    a base;
    a plurality of medicament cups, each cup adapted to containing a measured quantity of medicament therein and having an open upper end and a lower portion to be engaged;
    horizontal tables mounted on said base and having upper surfaces in alignment with each other, each table having opposing ends, one end of one table positioned adjacent an opposing end of another table in parallel relationship said plurality of medicament cups being placed in a row on each of said surfaces and slidable thereon;
    guide members respectively disposed along each row of the plurality of medicament cups the end portion of a guide member on one surface being aligned with the end portion of a guide member on an adjacent surface placed on said horizontal tables, said guide members having end portions;
    rotating members disposed between said ends of said horizontal tables adjacent said guide member end portions, each rotating member having a holding face in alignment with said upper surfaces and said end portions of said guide members of each respective horizontal table and having engaging means for engaging with said portion to be engaged of each medicament cup;
    a horizontal support shaft which is fixed to said rotating members and supported rotatably on said base so as to turn the rotating members simultaneously within a vertical plane perpendicular to direction of the row of said medicament cups;
    a turning mechanism mounted to said shaft for turning said horizontal supporting shaft;
    and a direct acting means for engaging each row of said plurality of cups placed on respective horizontal tables, for sliding the medicament cups in one direction along said guide members on said upper surface of the horizontal table, whereby the plurality of medicament cups on the horizontal tables are transferred one by one from the upper surface of one table onto the holding face of each rotating member and then onto the upper surface of an adjacent table.

2. An apparatus for automatically supplying medicament as set forth in claim 1, wherein each of the mentioned medicament cups is adapted with a flat leg part to be engaged, and each rotating member comprises:
    a holding block having a holding face and to which horizontal supporting shaft is fixed; and engaging means in which two side walls opposed in parallel to each other and a bottom wall connecting said two side walls are solidly formed to have a ⊐-shaped opening on upper part, and in which retaining claws in parallel to each other of and protruding toward opposite sides are solidly formed, whereby the engaging means engages with said holding block from outside in such a manner that said retaining claws are in parallel to said horizontal supporting shaft and that the engaging member be vertically slidable along the side walls of the holding block;
    spring means connected to said side walls for urging said engaging member downward with respect to said holding block; and
    a contact member attached to said base for pushing said engaging member upward with respect to said holding block against spring force of said spring means at the time of erecting the rotating members so as to form a gap for insertion of flat leg part of said medicament cup between said retaining claws of the engaging members and said holding face of the holding block.

3. An apparatus for automatically supplying medicament as set forth in claim 2, further comprising a guide member of which lower end face is open at a location right above the upper end opening of a test container disposed on the lower part and into which medicament is injected; said guide member comprising two side guide walls which are disposed on front side of each rotating member in parallel to a turning face of each rotating member and having a width slightly larger than that of a medicament cup; and a front shielding wall formed continuously on said two side guide walls.

4. An apparatus for automatically supplying medicament as set forth in claim 1, further comprising a guide member of which lower end face is open at a location right above the upper end opening of a test container disposed on the lower part and into which medicament is injected; said guide member comprising two side guide walls which are disposed on front side of each rotating member in parallel to a turning face of each rotating member and having a width slightly larger than that of a medicament cup; and a front shielding wall formed continuously on said two side guide walls.

* * * * *